United States Patent [19]

La Rosa

[11] 4,245,639

[45] Jan. 20, 1981

[54] SELF-INFLATING URINARY CATHETER

[75] Inventor: John F. La Rosa, West Kingston, R.I.

[73] Assignee: C. R. Bard, Inc., Murray Hill, N.J.

[21] Appl. No.: 34,754

[22] Filed: Apr. 30, 1979

[51] Int. Cl.³ ............................................ A61M 25/00
[52] U.S. Cl. .................................................. 128/349 B
[58] Field of Search ............ 128/348, 349 B, 349 BV, 128/218 P

[56] References Cited

U.S. PATENT DOCUMENTS

| 3,154,078 | 10/1964 | Goodrich, Jr. ...................... 128/348 |
| 3,211,151 | 10/1965 | Foderick et al. ................ 128/349 B |
| 4,074,714 | 2/1978 | Binard et al. ...................... 128/218 P |

*Primary Examiner*—John D. Yasko
*Attorney, Agent, or Firm*—Charles B. Smith; Robert R. Jackson

[57] ABSTRACT

A self-inflating urinary catheter which includes a retention balloon has a fluid reservoir communicating with the balloon, a wall in the reservoir comprising an elastic membrane arranged to retain fluid in an unpressurized state, a plunger arranged to depress the membrane into the fluid and initially displace part of the fluid and membrane through a window opening in one of the reservoir parts so as to stretch the membrane and pressurize the fluid, thereby exerting force on the fluid to expel if from the reservoir to inflate the retention balloon.

10 Claims, 13 Drawing Figures

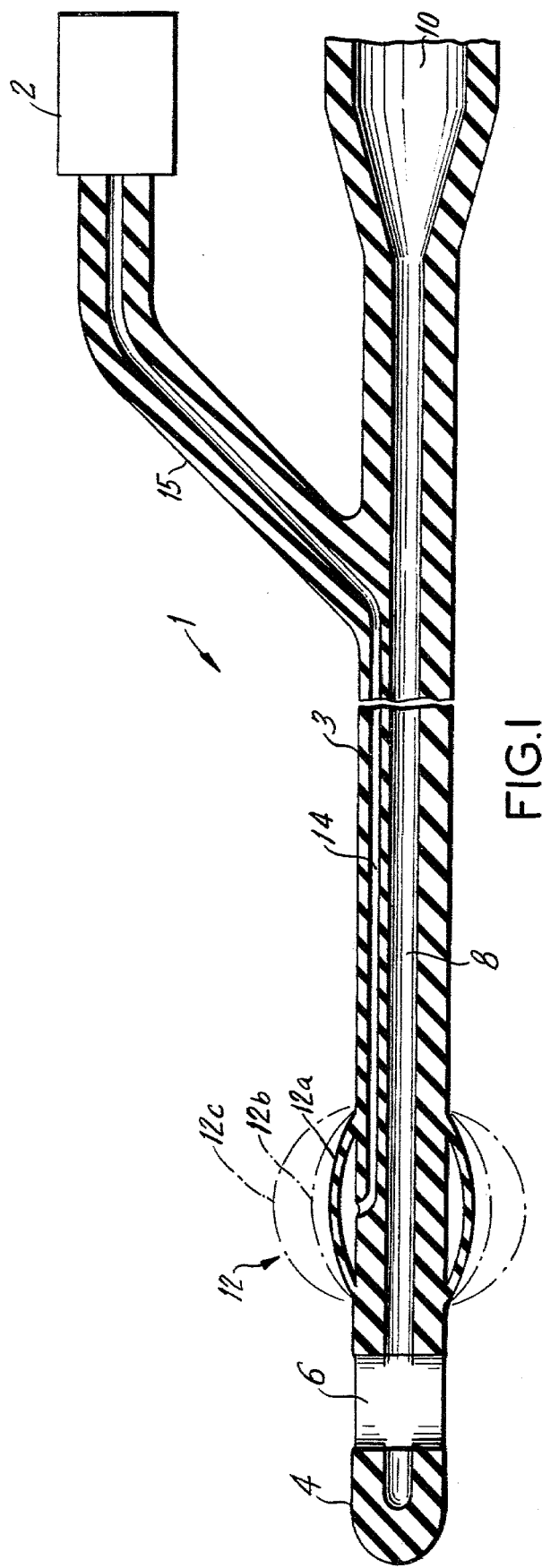
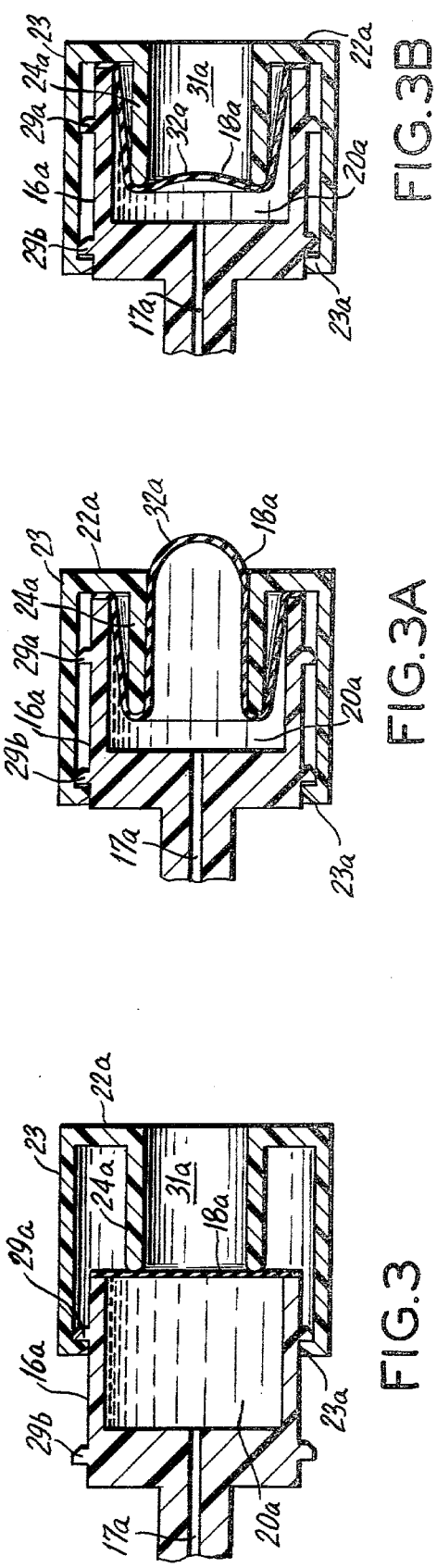

SELF-INFLATING URINARY CATHETER

BACKGROUND OF THE INVENTION

The retention of a urinary catheter in a human bladder so as to prevent it from slipping out during the period required to drain the bladder has been accomplished in several ways. The generally accepted so-called "Foley catheter" has a small inflatable balloon at its distal end (the end which is inserted) which is inflated to hold the distal end inside the bladder after the distal end has been inserted safely through the urethra and into the bladder. Inflation is accomplished by pumping a fluid into the balloon through an inflation lumen, a passage in the shaft of the catheter parallel to the drainage lumen or passage. The inflation fluid may be a gas or a liquid such as distilled water.

Current methods of inflating the balloon are susceptible to over- or under-inflation. Methods and devices for inserting the catheter and inflating the balloon are cumbersome and complicated. For instance, one such procedure is to insert the distal end of the catheter through the urethra into the bladder and at the same time to insert a syringe needle into the inflation lumen and then squeeze the syringe to inflate the balloon. This may require an operator and an assistant and may result in trauma to the patient if the balloon is inadvertently inflated while it is still within the urethra.

With any Foley catheter, means also have to be provided for deflating the retention balloon after use. Again, the deflation systems in present use are sometimes too complicated. This is often the case when the inflating device is a syringe and needle inserted into the inflation lumen. Deflation will again require such insertion of the syringe to withdraw the fluid. This may also be a two-handed operation, requiring a second person to hold the catheter.

So-called self-inflating catheters were developed to try to solve these problems, but they have had problems of their own. A number of arrangements have been tried to provide a reservoir, integral with the catheter, for storage of inflation fluid under pressure ready to be expelled to inflate the retention balloon. But such systems have not thus far met the requirements for satisfactory performance.

Such requirements are that the catheter have a long shelf-life under sanitary conditions, that it be immediately ready for use, that it be simple to operate by one person and that it be inexpensive to produce as a throwaway item. Its arrangement must also be such that the retention balloon is capable of deflation and reinflation if the instrument is prematurely inflated before its desired placement with the distal end in the bladder.

A widely used type of self-inflating catheter has an over-inflated rubber reservoir in which the fluid is retained by a clamp under pressure during storage. After insertion of the catheter into the bladder, the clamp is removed to inflate the retention balloon. During storage, however, the stretched reservoir walls tend to lose their restoring force because they "take a set" and "lose memory" so that when the clamp is removed, the rubber reservoir does not exert enough force to inflate the balloon. Also, once such a system is activated to inflate the retention balloon, there is no way of deflating and reinflating the balloon in case the catheter is not properly placed in the first instance. There is also no adequate way of determining how much of the fluid has been dispersed from the reservoir at any instant. Another problem is that when the fluid is thus stored under pressure, considerable loss of fluid occurs through the stretched reservoir walls during storage. This reduces the amount by which the retention balloon may be inflated, and in some cases so much fluid is lost that no inflation occurs in use.

The principal objects of this invention are therefore to provide in an inexpensive urinary catheter a retention balloon inflation system in which no fluid loss occurs, which will allow the retention balloon to be deflated and reinflated and which will provide a visual indicator of the degree of inflation at any instant.

SUMMARY OF THE INVENTION

These and other objects of the invention are accomplished by providing a self-inflating catheter having a fluid reservoir connected through the inflation lumen to the retention balloon which is at the distal end of the catheter to be inserted through the urethra and into the bladder of the patient. The inflation lumen is a passage in the shaft of the catheter running parallel to the drainage lumen which is the main passage in the shaft of the catheter through which the fluid is drained from the bladder into a suitable receptacle outside of the patient.

The reservoir structure of the invention has a substantially rigid body part and an elastic or elastomeric membrane forming at least one wall portion of the reservoir retaining the inflation fluid. This membrane may be in the form of a diaphragm or of a partial or total bulb or bag or balloon-like conformation. The terms wall portion, membrane and diaphragm as used herein are intended to cover all such forms. The reservoir is filled with enough fluid for the purpose of subsequently inflating the retention balloon, but not so much as to initially put the elastic membrane under any substantial tension. Therefore, prior to use of the catheter, the fluid in the reservoir is unpressurized.

A substantially rigid plunger part is arranged to be depressed against and into the elastic membrane, thereby placing the membrane under tension in a stretched condition and pressurizing the fluid. In addition, part of the membrane (and the contained fluid) is at least momentarily displaced into a bulbous form which then extends through and protrudes from at least one window opening in one of the rigid parts of the reservoir. Because the membrane is now stretched and under tension and is trying to contract, it starts to expel the fluid from the reservoir through a restricted passage into the inflation lumen and thence into the retention balloon thus inflating the balloon.

The plunger may be held depressed under pressure against the diaphragm by the hand of the operator, but preferably a releasable retention lock is provided to hold the plunger in depressed position to keep the diaphragm under tension until the fluid has been expelled sufficiently to inflate the retention balloon. The purpose of the restricted passage is to provide an elapse of time between the initial operation of the plunger and the completion of expulsion of the fluid from the reservoir into the balloon.

As will be shown, the arrangement may take several forms. The pressurized bulbous part of the membrane which has been placed under tension may be received into a hollow portion of the plunger forming the window opening or it may be expanded outwardly through an opening which may be one or more windows in the rigid body part of the reservoir. The reservoir body may be cylindrical, rectangular, oval or of other desirable shape.

Further features of the invention, its nature, and various advantages will be more apparent from the accompanying drawing and the following detailed description of the invention.

BRIEF DESCRIPTION OF THE DRAWING

FIG. 1 is a longitudinal, partly fragmented, sectional view of a self-inflating catheter of which the present invention is an improvement, with the improved part indicated schematically to show general relationships.

FIG. 3 is a partial longitudinal sectional view showing an alternate embodiment of the inflation apparatus of the invention with the reservoir unpressurized and the diaphragm relaxed.

FIG. 3A is a view similar to FIG. 3 showing the fluid in the reservoir pressurized and the diaphragm stretched.

FIG. 3B is a view similar to FIG. 3 showing the reservoir fluid expended and the diaphragm in its final configuration.

DETAILED DESCRIPTION OF THE INVENTION

Figure 2:
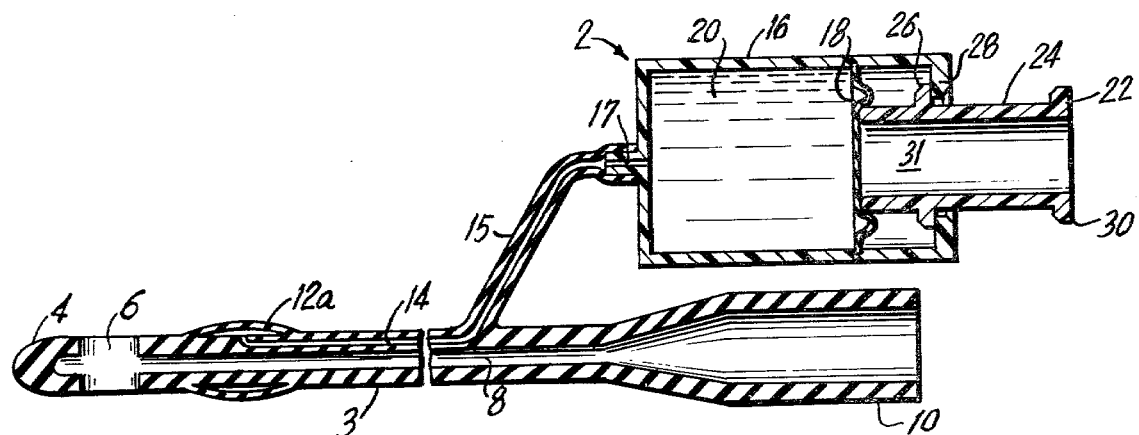
FIG. 2 is a longitudinal, partly fragmented, sectional view showing one embodiment of the improved inflation apparatus of the invention with the reservoir full of unpressurized fluid, the diaphragm relaxed and the retention balloon deflated prior to use.

A self-inflating urinary catheter of the type of which this invention is an improvement is indicated at 1 in FIG. 1. The improved inflation apparatus of the invention is schematically indicated at 2 and its details and various forms will be further described and shown.

The catheter shown in FIG. 1 is the "Foley catheter" mentioned above. It comprises a long narrow resilient cylindrical shaft 3 made of latex or silicone rubber and with one end 4, called the distal end, rounded off. This is to facilitate its insertion into and through the urethra and into the bladder of the patient for the purpose of draining fluids from the bladder which have become blocked or dammed up due to a pathology suffered by the patient. The distal end 4 has an opening 6 connected to a longitudinal passage 8 called the drainage lumen for conducting drained fluids toward or to the other end or proximal end 10 of the catheter 1 where the drainage lumen 8 may be connected to a tube leading to a container, not shown, outside of the patient.

Adjacent the opening 6 at the distal end 4 is a retention balloon 12 completely surrounding and sealed to the shaft 3 of the catheter. An inflation lumen 14 in the shaft of the catheter leads from inside the balloon 12 lengthwise of the shaft to the inflation apparatus 2 which is usually in a branch 15 formed at the proximal end of the catheter to separate the drainage lumen 8 from the inflation lumen 14 at that end outside the patient.

While the distal end 4 is being inserted through the urethra and into the bladder, the retention balloon 12 is deflated and relaxed. After the distal end 4 and the balloon 12 have entered into the bladder, the inflation apparatus 2 is operated to allow fluid from a reservoir in or associated with the apparatus 2 to pass under sufficient pressure through the inflation lumen 14 to inflate the balloon 12 into a condition indicated by the dotted line 12c. Hereinafter, the relaxed or deflated condition of the balloon 12 will be indicated as 12a, a partially inflated condition will be indicated as 12b and a completely inflated condition as 12c.

Figure 2A:
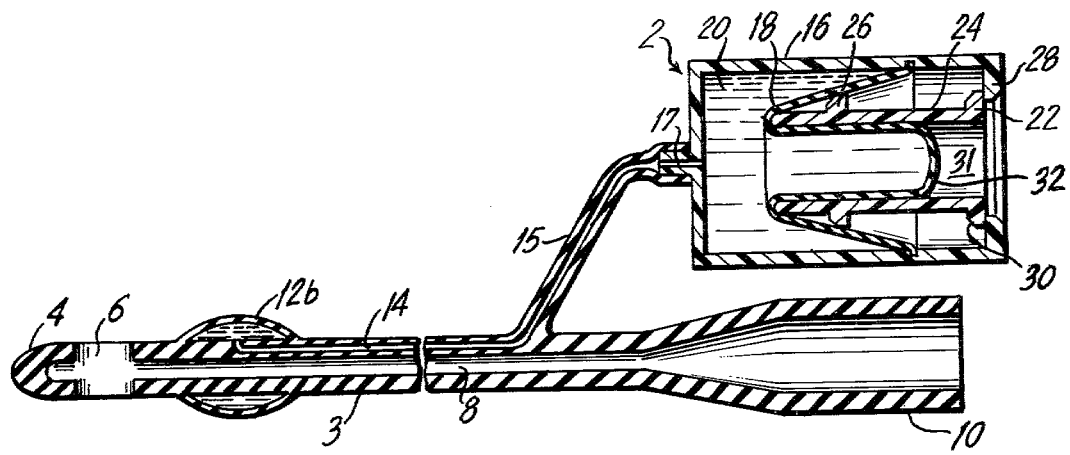
FIG. 2A is a view similar to FIG. 2 showing the reservoir pressurized and the diaphragm stretched under tension for inflating the retention balloon and with the balloon partially inflated.
Figure 2B:
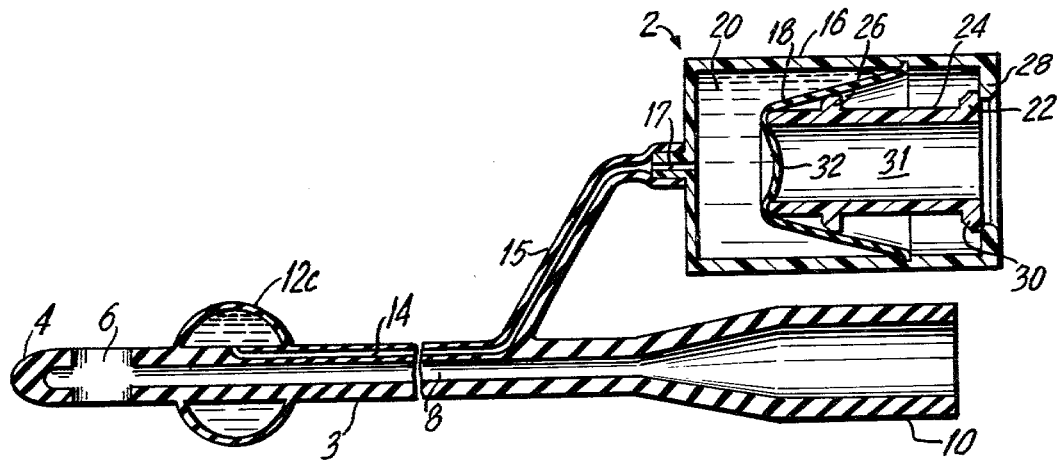
FIG. 2B is a view similar to FIG. 2 showing the reservoir fluid expended, the diaphragm in its final configuration and the retention balloon completely inflated.

A first embodiment of the improved inflation apparatus of this invention is shown in FIGS. 2, 2A and 2B in which reference numerals used in FIG. 1 are used to indicate corresponding parts. In this embodiment the inflation apparatus 2 comprises a reservoir structure which includes a substantially rigid cylinder 16, the interior of one end of which is connected through a small diameter passage 17 to the inflation lumen 14. Toward the other end of the cylinder 16 is a flexible diaphragm or membrane 18 sealed at its periphery to the inner surface of cylinder 16 and enclosing a major portion of the interior of the cylinder to form the inflation fluid reservoir. Membrane 18 is an elastic or elastomeric member of rubber, silicone or other fluid-proof stretchable material. In the condition shown in FIG. 2, the reservoir is filled with a fluid 20 in an unpressurized state with the elastic diaphragm 18 in a relaxed and unstretched and unstressed condition as shown. Such a fluid may preferably be distilled water, but may also be any other liquid or gas suitable for the purpose.

Seated in the right hand end of the reservoir cylinder 16 is a plugner 22 having a hollow cylindrical portion 24. The plunger is retained within the reservoir cylinder 16 by a radially outwardly extending part 26 on its portion 24 and a radially inwardly extending part 28 of the cylinder 16.

In the condition shown in FIG. 2 with the balloon deflated as shown at 12a, the catheter may be inserted into the patient. When the distal or left end 4 with its drainage opening 6 and the balloon 12a have entered into the bladder, the operator depresses the plunger 22 to the left until it reaches the condition shown in FIG. 2A where it may be held by the operator and then locked in place by engagement of the inwardly extending retention part 28 of the cylinder 16 with the outer rim 30 of the plunger, thus providing a releasable detent type of catch or retention lock. Such a releasable detent feature may be provided for the lock, for example, as by providing engageable parts which are resilient and releasable from each other or by forming them as intermittent protuberances or lugs which can be engaged or disengaged by turning the plunger 22 slightly relative to the cylinder 16.

With the plunger 22 in the condition shown in FIG. 2A, diaphragm 18 is placed under stress and stretched so that its central portion is displaced into a window opening 31 formed by the hollow center of the plunger part 24 thus forming a bulbous part 32 in the diaphragm, the stretching of which along with the outside stretched parts of the diaphragm 18 exerts pressure on the fluid 20 in the reservoir. The momentary formation of a bulb in the diaphragm 18 results because the passage 17 from the reservoir to the inflation lumen 14 is formed with a relatively small diameter. Nevertheless, as soon as the plunger 22 is depressed into the condition shown in FIG. 2A the liquid starts to be expelled from the reservoir through the passage 17 and 14 to inflate the balloon 12 which is thus shown in partially inflated condition 12b in FIG. 2A.

When the balloon 12 has been completely inflated into the condition shown as 12c in FIG. 2B, the fluid 20 remaining in the reservoir becomes relatively less pressurized and the stressed bulb portion 32 becomes relatively more relaxed as shown in FIG. 2B.

In the embodiments shown in FIGS. 2, 2A and 2B, the bulbous form 32 of the diaphragm 18 created when the plunger is depressed can be observed through the open end of the plunger to provide an indication of the degree of expulsion of the fluid 20 from the reservoir and of resulting inflation of the balloon 12.

It will be apparent that this embodiment, as well as the others disclosed herein, are called self-inflating because when the plunger 22 is depressed and locked, the balloon has not yet inflated. Therefore it is essentially the pressure caused by the stressing and stretching of the diaphragm or membrane 18 after depression of the plunger 22 which creates a self-inflating condition.

It will also be apparent that if inflation of the balloon 12 should occur prematurely, deflation can easily be accomplished by releasing the plunger 22 to allow it to move out again to its original condition to the right, allowing deflation of the balloon 12 and refilling of the reservoir.

A second alternative embodiment is shown in FIGS. 3, 3A and 3B. As shown in these Figures, the principal difference from the embodiment shown in FIGS. 2, 2A and 2B is in the shape of the plunger, here designated by 22a. This plunger 22a has a hollow cylindrical part 24a arranged to be depressed against a diaphragm 18a in the reservoir cylinder 16a to produce the stressed bulbous portion 32a extending through the window opening 31a as shown in FIG. 3A. In FIG. 3B, what was the bulbous portion 32a in FIG. 3A is again substantially relaxed after expulsion of the fluid 20a from the reservoir.

The difference in the plunger 22a from the plunger 22 in FIG. 2 is that the plunger 22a has an outer cylindrical housing 23 which is slideable over the outer surface of the reservoir cylinder 16a. The reservoir cylinder 16a has outwardly extending radial parts 29a and 29b for locking engagement with a radially inwardly extending part 23a integral with the plunger housing 23. The locking part 29a retains the plunger 22a on the reservoir housing 16a in retracted condition and the radial part 29b engages the part 23a to retain the plunger locked in depressed condition until released by the operator. Otherwise the function and operation of the plunger 22a are the same as for the plunger 22 in FIGS. 2, 2A and 2B. Because the plunger 22a is formed with an opening at the outer right hand end of the cylindrical inner portion 24a, the condition of the stretched bulbous portion 32a of the diaphragm 18a can readily be observed directly through the cylindrical inner opening as seen in FIGS. 3A and 3B to provide a clear visual indication as to the condition of expulsion of the fluid 20a from the reservoir 16a.

Figure 4:
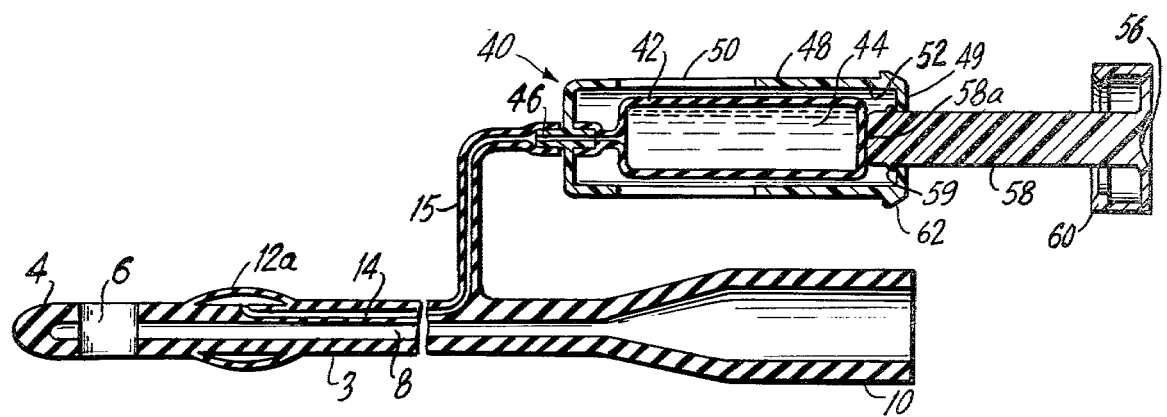
FIG. 4 is a longitudinal, partly fragmented, sectional view showing another embodiment of the inflation apparatus of the invention with the reservoir unpressurized, the diaphragm (in this case the entire reservoir) relaxed and the retention balloon deflated.
Figure 4A:
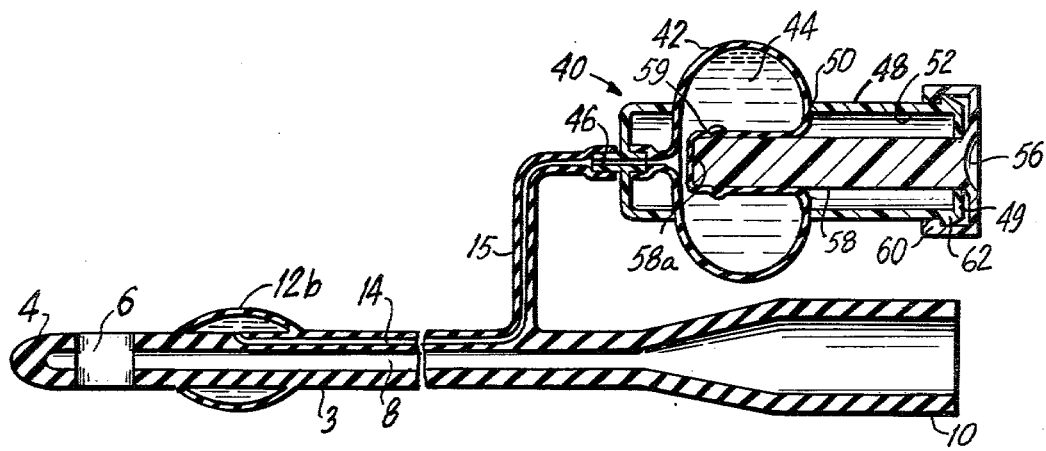
FIG. 4A is a view similar to FIG. 4 showing the reservoir pressurized and the diaphragm stretched under tension and with the retention balloon partially inflated.
Figure 4B:
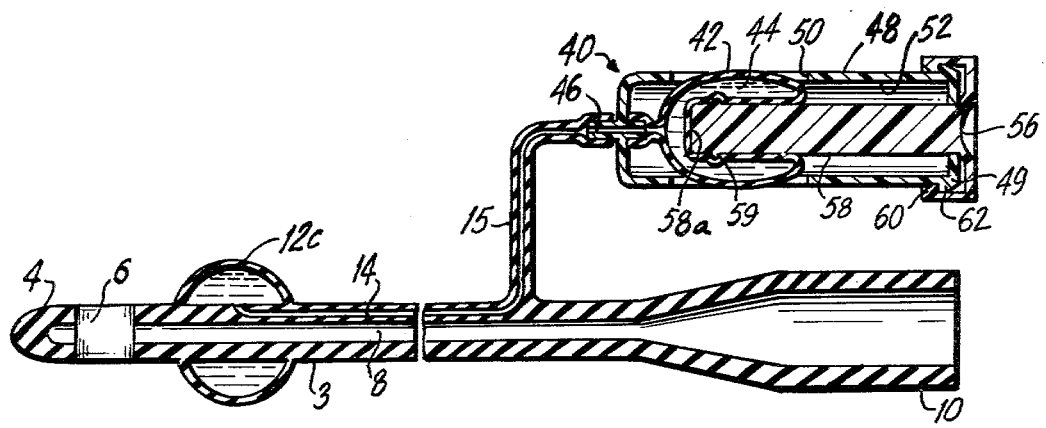
FIG. 4B is a view similar to FIG. 4 showing the reservoir fluid expended, the diaphragm in its final configuration and the retention balloon completely inflated.

A third alternative embodiment is indicated at 40 in FIGS. 4, 4A and 4B. This is a reservoir structure including an elastomeric diaphragm or membrane in the form of an enclosed bag 42 containing inflation fluid 44 in an unpressurized state as seen in FIG. 4. The reservoir bag 42 is connected to a restricted passage 46 which, in turn, is connected to the inflation lumen 14.

The elastomeric reservoir bag 42 is contained within a substantially rigid body part or housing 48 which has two or more window openings 50 in its cylindrical surface extending parallel to the axis of the housing 48. In its relaxed and unstretched state, the elastomeric reservoir 42 is disposed in a substantially cylindrical shape within the confines of the interior cylindrical walls 52 of the housing 48.

A substantially rigid plunger part 56 having a cylindrical portion 58 is arranged to slide longitudinally within the interior wall 52 of the cylindrical housing 48 and with its end 58a impinging against the right hand end of the elastic reservoir 42. Plunger 56 is guided by inwardly projecting part 49 on the end of housing 48 and is retained in housing 48 by a retention ring 59 on cylindrical portion 58 cooperating with part 49.

In operation, with the reservoir 42 filled with fluid 44, when the plunger 56 is depressed to the left against the wall of the reservoir 42, the side walls of the reservoir membrane 42 are deformed so as to be displaced outwardly through the windows 50 to stretch the walls of the membrane 42 and place the fluid 44 under pressure as seen in FIG. 4A, thus starting to expel the liquid 44 through the restricted passage 46 into the inflation lumen 14 and thence into the balloon 12b.

The plunger 56 is locked into position by engagement of its peripheral portions 60 with corresponding peripheral portions 62 at the end of the substantially rigid housing 48. This locking mechanism may be disengaged as by deforming resilient portions of either of the locking members 60 and 62 or by arranging them in a circumferentially intermittent manner so as to disengage them by turning one part with respect to the other.

When the fluid 44 has been expelled to completely inflate the balloon 12c, the parts are in the condition shown in FIG. 4B with the elastomeric reservoir membrane 42 substantially relaxed back into a double up shape substantially within the inner wall 52 of the housing 48.

Figures 5, 5A, 5B:
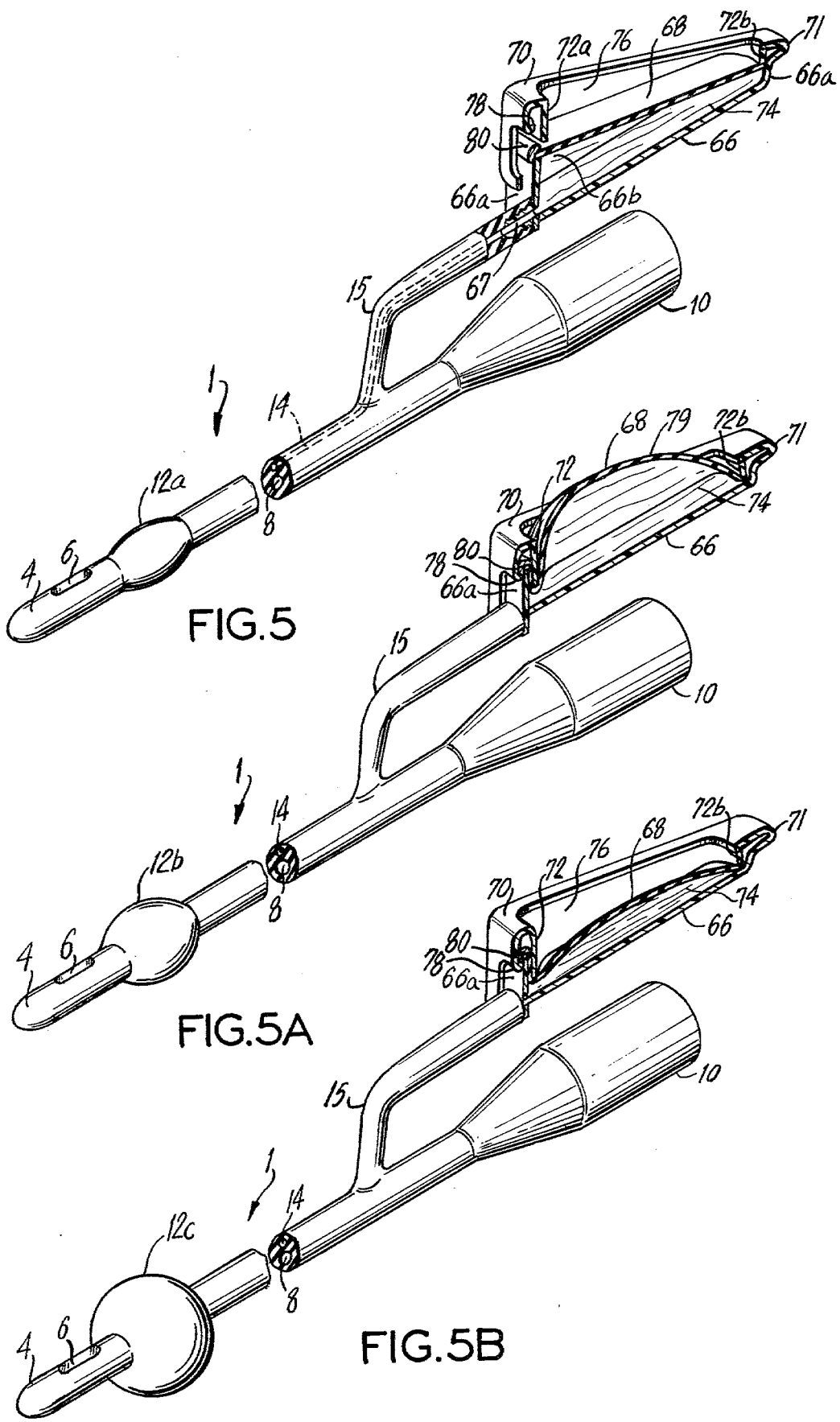
FIG. 5 is a perspective view, partly fragmented and partly in section, showing still another alternate embodiment of the improved inflation apparatus of the invention with the reservoir and its diaphragm in relaxed unpressurized condition prior to operation.
FIG. 5A is a view similar to FIG. 5 showing the plunger depressed and with the diaphragm in stressed condition and with the reservoir pressurized.
FIG. 5B is a view similar to FIG. 5 with the fluid expelled from the reservoir, the diaphragm in its final configuration and the retention balloon completely inflated.

A fourth alternative embodiment is shown in FIGS. 5, 5A and 5B. In this embodiment the reservoir structure 66 comprises a substantially rigid housing or body part having end walls 66a and side walls 66b (one of the latter having been cut away and not shown). The top wall of the reservoir 66 is a rectangular shaped elastomeric diaphragm 68. A correspondingly shaped substantially rigid plunger part 70 is hinged at 71 to one of the end walls 66a, preferably by being formed integrally with it in a manner to provide a hinging action. The plunger 70 has downwardly extending protrusions 72a and 72b which are arranged to impinge against the elastomeric diaphragm 68.

In the condition shown in FIG. 5, the diaphragm 68 is relaxed with the fluid 74 under it in unpressurized condition.

In FIG. 5A the catheter has been inserted and the plunger 70 has been pressed downwardly against the diaphragm 68 thus displacing the central portion of the diaphragm upwardly through a window opening 76 in the top of the plunger 70 and forming a bulbous protrusion 79. With the plunger 70 depressed, the fluid 74 in the reservoir is pressurized and flows through restricted passage 67 to the inflation lumen of the catheter to inflate the balloon 12b.

The plunger 70 may be locked temporarily downwardly by engagement of a lip 78 on its end with a protrusion 80 on one end 66a of the reservoir 66. The lip 78 may be made resilient and easily separable from the protrusion 80 to disengage the plunger 70.

The condition of the parts with the fluid 74 fully expended from the reservoir 66 and into the balloon 12c and with the bulbous portion 79 of the diaphragm 68 relatively relaxed down into place again is shown in FIG. 5B.

Because the inflation fluid remains unpressurized during storage prior to use, it does not tend to migrate through the walls of the reservoir membrane and other parts as readily as if it were pre-pressurized. Therefore, the reservoir parts may be made of thinner and less expensive material and a greater variety of materials is available for use.

The catheter balloon may be easily deflated and reinflated during use, and its condition of inflation is readily ascertainable by observing the degree of deflation of the reservoir.

I claim:

1. A self-inflating urinary catheter of the type which includes a retention balloon and an inflation lumen connected for conducting fluid to inflate the balloon, wherein the improvement comprises a fluid reservoir structure connected to the inflation lumen, said reservoir structure including a substantially rigid body part, a substantially rigid plunger part and an elastic membrane, at least one of said substantially rigid parts having at least one window opening, said elastic membrane being arranged to retain fluid in the reservoir in an initially unpressurized state, said plunger part being arranged to depress the membrane into the fluid thereby at least momentarily displacing part of the fluid and membrane through the window opening so as to stretch the membrane and pressurize the fluid, said stretched membrane thereby exerting force on the fluid to expel it out of the reservoir structure and through the inflation lumen to inflate the retention balloon, said plunger part being engagable with the body part when operated to depress the membrane so that the membrane continues to exert force on the fluid without continued application of force by the user to any portion of the apparatus.

2. A self-inflating urinary catheter according to claim 1 in which at least a portion of the stretched membrane and pressurized fluid are visible to provide an indication of the amount of fluid remaining in the reservoir structure before its expulsion to inflate the retention balloon.

3. A self-inflating urinary catheter according to claim 1 in which the engagement between the plunger part and the body part is releasable to allow the membrane to return to its initial condition and thereby remove the force on the fluid.

4. A self-inflating urinary catheter according to claim 1 in which the reservoir structure comprises a substantially rigid cylinder with one end connected to the inflation lumen and with the membrane disposed toward the other end and enclosing the interior of the cylinder and with the plunger part arranged to be moved within said other end of the cylinder to impinge against the membrane and fluid.

5. A self-inflating urinary catheter according to claim 4 in which the plunger part has a window opening at its inner end for receiving a bulbous displaced portion of the fluid and membrane when the plunger is moved to impinge against the membrane and fluid.

6. A self-inflating urinary catheter according to claim 1 which includes means by which to view the displaced part of the fluid and membrane as an indication of the degree of epulsion of fluid from the reservoir.

7. A self-inflating urinary catheter of the type which includes a retention balloon and an inflation lumen connected for conducting fluid to inflate the balloon, wherein the improvement comprises a fluid reservoir structure including an elastic membrane in the form of an enclosed bag connected to the inflation lumen, a substantially rigid body part in the form of a housing containing said bag, and a substantially rigid plunger part, said housing having at least one window opening, said bag being arranged to retain fluid in the reservoir in an initially unpressurized state, said plunger part being arranged to depress a portion of the bag into the fluid thereby at least momentarily displacing part of the fluid and the bag through the window opening in the housing so as to stretch the bag and pressurize the fluid, said stretched bag thereby exerting force on the fluid to expel it out of the reservoir structure and through the inflation lumen to inflate the retention balloon.

8. A self-inflating urinary catheter of the type which includes a retention balloon and an inflation lumen connected for conducting fluid to inflate the balloon, wherein the improvement comprises a fluid reservoir structure connected to the inflation lumen, said reservoir structure including a substantially rigid body part, a substantially rigid plunger part having a window opening and an elastic membrane, said elastic membrane being arranged to retain fluid in the reservoir in an initially unpressurized state, said plunger part being arranged to depress the membrane into the fluid, thereby at least momentarily displacing a portion of the fluid and membrane through the window opening in the plunger part so as to stretch the membrane and pressurize the fluid, said stretched membrane thereby exerting force on the fluid to expel it out of the reservoir structure and through the inflation lumen to inflate the retention balloon.

9. A self-inflating urinary catheter according to claim 1 in which the plunger part is hinged to the wall of the reservoir.

10. A self-inflating urinary catheter according to claim 1 which includes a restricted passage between the reservoir structure and the retention balloon thereby providing an elapse of time between the initial stressing of the membrane and the completion of expulsion of the fluid from the reservoir structure into the balloon.

* * * * *